(12) United States Patent
Lin et al.

(10) Patent No.: US 11,833,183 B2
(45) Date of Patent: Dec. 5, 2023

(54) METHOD FOR IMPROVING BODY SHAPE AND IMPROVING SKIN CONDITION USING NONI FRUIT FERMENT

(71) Applicant: TCI CO., LTD., Taipei (TW)

(72) Inventors: Yung-Hsiang Lin, Taipei (TW); Pei-Yi Wu, Taipei (TW)

(73) Assignee: TCI CO., LTD., Taipei (TW)

( * ) Notice: Subject to any disclaimer, the term of this patent is extended or adjusted under 35 U.S.C. 154(b) by 0 days.

(21) Appl. No.: 17/585,612

(22) Filed: Jan. 27, 2022

(65) Prior Publication Data

US 2023/0022490 A1    Jan. 26, 2023

Related U.S. Application Data

(60) Provisional application No. 63/221,010, filed on Jul. 13, 2021.

(30) Foreign Application Priority Data

Dec. 29, 2021    (TW) .................................. 110149501

(51) Int. Cl.
| | |
|---|---|
| *A61K 36/746* | (2006.01) |
| *A61P 17/18* | (2006.01) |
| *A61P 1/14* | (2006.01) |
| *A61K 36/06* | (2006.01) |
| *A61K 35/747* | (2015.01) |
| *A61P 3/04* | (2006.01) |
| *A61K 35/00* | (2006.01) |

(52) U.S. Cl.
CPC .......... *A61K 36/746* (2013.01); *A61K 35/747* (2013.01); *A61K 36/06* (2013.01); *A61P 1/14* (2018.01); *A61P 3/04* (2018.01); *A61P 17/18* (2018.01); *A61K 2035/115* (2013.01)

(58) Field of Classification Search
None
See application file for complete search history.

(56) References Cited

FOREIGN PATENT DOCUMENTS

CN    110577657 A    * 12/2019    ............. A61P 39/06

OTHER PUBLICATIONS

Inada et. al. (*Morinda citrifolia* Linn. (Noni) and is Potential in Obesity-Related Metabolic Dysfunction, Nutrients, 2017, 9, 540;1-29) (Year: 2017).*
Congying et. al. (Isolation, Identification and Fermentation Characteristics of Acetic Acid Bacteria from Naturally Fermented Noni (*Morinda citrifolia* L.) Juice, Food Science, vol. 40, Issue 12, 131-136, 2019) (Year: 2019).*
Polo et. al. (Role of Ground and Excited Singlet State Oxygen in the Red Light-Induced Stimulation of *Escherichia coli* Cell Growth, Biochemical and Biophysical Research Communications, vol. 257, No. 3, 1999). (Year: 1999).*
Xiaojuan et. al. (CN110577657A) (Year: 2019).*
Kowpong "Microbial succession in a fermenting of wild forest noni (*Morinda coreia* Ham) fruit plus molasses and its role in producing a liquid fertilizer", Electronic Journal of Biotechnology, 2009, vol. 12, issue 3, Abstract. (Year: 2009).*
Kowpong "Microbial succession in a fermenting of wild forest noni (*Morinda coreia* Ham) fruit plus molasses and its role in producing a liquid fertilizer", Electronic Journal of Biotechnology, 2009, vol. 12, issue 3, pp. 1-11. (Year: 2009).*

* cited by examiner

*Primary Examiner* — Terry A McKelvey
*Assistant Examiner* — Jacob A Boeckelman
(74) *Attorney, Agent, or Firm* — Chieh-Mei Wang

(57) ABSTRACT

A method for improving body shape and improving skin condition using a noni fruit ferment is provided, and the method includes: administrating a composition to a subject in need thereof. The composition includes an effective amount of noni fruit ferment. The noni fruit ferment is prepared by (a) mixing glucose and noni fruit with water for extraction, to obtain a noni fruit broth, and (b) fermenting the noni fruit broth with a plurality of bacteria strains. The bacteria strains include yeast, lactic acid bacteria, and acetic acid bacteria. In step (b), the noni fruit broth and the bacteria strains are irradiated with a red light source with a wavelength of 620 nm to 750 nm. In addition, the noni fruit ferment also has at least one of the following functions: removing free radicals, improving defecation status, and improving gastrointestinal motility.

10 Claims, 11 Drawing Sheets
Specification includes a Sequence Listing.

000
METHOD FOR IMPROVING BODY SHAPE AND IMPROVING SKIN CONDITION USING NONI FRUIT FERMENT

CROSS-REFERENCES TO RELATED APPLICATIONS

This application claims the benefit of U.S. provisional application Ser. No. 63/221,010, filed on Jul. 13, 2021 and claims the priority of Patent Application No. 110149501 filed in Taiwan, R.O.C. on Dec. 29, 2021. The entirety of the above-mentioned patent applications is hereby incorporated by references herein and made a part of the specification.

REFERENCE OF AN ELECTRONIC SEQUENCE LISTING

The contents of the electronic sequence listing (P212221US1_ST25.txt; Size: 1.81 KB; and Date of Creation: Jan. 18, 2022) is herein incorporated by reference in its entirety.

BACKGROUND

Technical Field

The present invention relates to a method using a noni fruit ferment, and in particular, to a method for improving body shape and improving skin condition using a noni fruit ferment.

Related Art

*Morinda citrifolia*, also referred to as great *morinda* and Indian mulberry, is a plant of the genus *Morinda* in the family Rubiaceae, which is a shrub to a small tree with a height of 1 m to 5 m, and belongs to coffee economic crops. The fruit of *Morinda citrifolia* is referred to as noni fruit. The noni fruit is abundant in the South Pacific Islands. It is an oval compound fruit of about 4 cm to 7 cm in size, with many uneven pockmarks distributed on the surface. The noni fruit is green at first, then turns yellow, and is almost white when ripe. There are a number of seeds inside the fruit. The noni fruit has plenty of juice, but it has a strong odor and bitterness.

SUMMARY

In view of this, it is necessary to research or develop a natural plant ingredient, noni fruit, and prepare a natural plant product beneficial to the human body from it.

Based on this, in some embodiments, a method for improving body shape is provided, and the method comprises: administrating to a subject in need thereof a composition comprising an effective amount of noni fruit ferment. The noni fruit ferment is prepared by (a) mixing glucose and noni fruit with water for extraction, to obtain a noni fruit broth, and (b) fermenting the noni fruit broth with a plurality of bacteria strains, to obtain the noni fruit ferment. The bacteria strains comprise yeast, lactic acid bacteria, and acetic acid bacteria. In the step (b), the noni fruit broth and the bacteria strains are irradiated by a red light source with a wavelength of 620 nm to 750 nm.

In some embodiments, the improving body shape is at least one of increasing whole body muscle mass, reducing whole body fat percentage, reducing belly fat mass and/or leg fat mass, reducing subcutaneous fat mass and/or visceral fat mass, and reducing waist circumference.

In some embodiments, the noni fruit ferment contributes to the improving body shape by at least one of promoting leptin production and promoting fat metabolism.

In some embodiments, the noni fruit ferment contributes to the promoting fat metabolism by increasing the expression level of one or more fat loss genes.

In some embodiments, the one or more fat loss genes are at least one of adipose triglyceride lipase (ATGL) gene, lipase E (LIPE) gene, and uncoupling protein 1 (UCP1) gene.

In addition, in some embodiments, a method for improving skin condition is further provided, and the method comprises: administrating to a subject in need thereof a composition comprising an effective amount of noni fruit ferment. The noni fruit ferment is prepared by (a) mixing glucose and noni fruit with water for extraction, to obtain a noni fruit broth, and (b) fermenting the noni fruit broth with a plurality of bacteria strains, to obtain the noni fruit ferment. The bacteria strains comprise yeast, lactic acid bacteria, and acetic acid bacteria. In the step (b), the noni fruit broth and the bacteria strains are irradiated by a red light source with a wavelength of 620 nm to 750 nm. The improving skin condition is at least one of reducing skin redness, improving skin elasticity, and reducing sun spots.

In some embodiments, the noni fruit ferment contributes to the improving skin elasticity by promoting elastin production.

In some embodiments, the noni fruit ferment also has at least one of the following functions: removing free radicals, improving bowel movement, and improving gastrointestinal motility.

In some embodiments, the glucose is added in an amount of 2 wt % to 8 wt % of a total weight of the noni fruit and the water.

In some embodiments, a weight of the water is 3 folds to 5 folds of a total weight of the noni fruit.

In some embodiments, relative to the noni fruit broth, the yeast is added in an amount of 0.01 wt % to 0.5 wt %, the lactic acid bacteria are added in an amount of 0.01 wt % to 0.25 wt %, and the acetic acid bacteria are added in an amount of 1 wt % to 20 wt %.

In some embodiments, a fermentation time is 24 hours to 72 hours for the yeast, a fermentation time is 24 hours to 72 hours for the lactic acid bacteria, and a fermentation time is 72 hours to 240 hours for the acetic acid bacteria.

In some embodiments, the noni fruit ferment has a pH value of 2.7 to 3.7 and a Brix degree of 23 to 27.

Based on the above, in any embodiment, the noni fruit ferment may provide at least one of the following functions: improving body shape and improving skin condition, so as to be further prepared as a composition with corresponding functions. In some embodiments, the improving body shape may be at least one of increasing whole body muscle mass, reducing whole body fat percentage, reducing belly fat mass and/or leg fat mass, reducing subcutaneous fat mass and/or visceral fat mass, and reducing waist circumference. In addition, in some embodiments, the improving body shape may be achieved by promoting leptin production and/or promoting fat metabolism. In some embodiments, the promoting fat metabolism may be achieved by increasing an expression level of fat loss gene. In some embodiments, the promoting fat metabolism may also be achieved by increasing an expression level of at least one of adipose triglyceride lipase (ATGL) gene, lipase E (LIPE) gene, and uncoupling protein 1 (UCP1) gene. In some embodiments, the improving skin condition may be at least one of reducing skin redness, improving skin elasticity, and reducing sun spots. In addition, in some embodiments, the improving skin elasticity may be achieved by promoting elastin production. In addition, in some embodiments, the noni fruit ferment may further have at least one of the following functions: removing free radicals, improving defecation status, and improving gastrointestinal motility, so as to be further prepared as a composition with corresponding functions.

DETAILED DESCRIPTION

Figure 1:
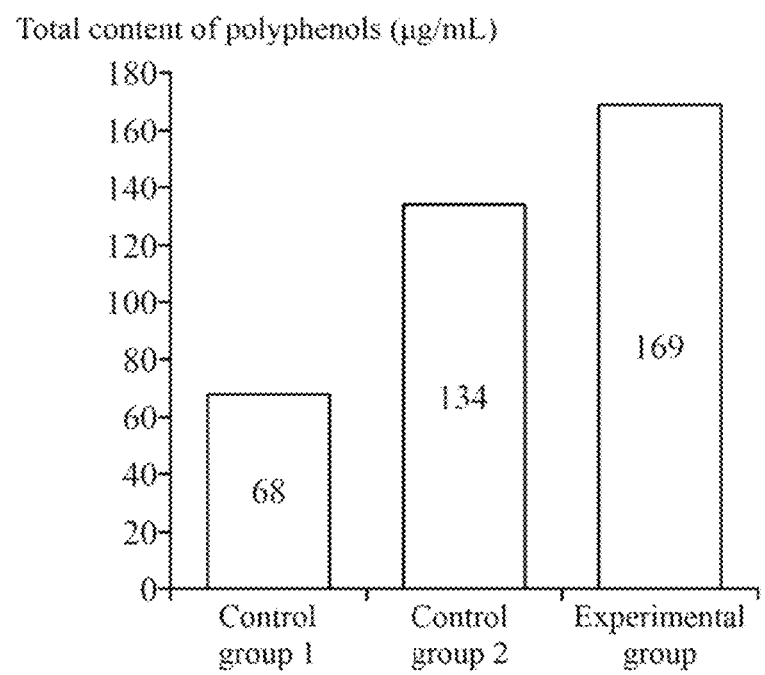
FIG. 1 is a diagram showing detection results of a total polyphenol content of a noni fruit ferment prepared by the method in Example 1.

Numerical values used herein are approximate values, and all experimental data are expressed within the range of ±10%, and best within the range of ±5%.

Herein, the term "wt %" refers to weight percentage, and the term "vol %" refers to volume percentage.

Herein, the term "Brix degree" (symbol ° Bx) is a unit for measuring the sugar content, which represents grams of sucrose per 100 g of solution at 20° C.

Herein, the term "broth" refers to a product obtained through extraction. The broth may be a solution obtained by dissolving a solute in a solvent, or may be a solvent-free or substantially solvent-free concentrate.

Herein, the term "ferment" refers to an active ingredient formed by subjecting a broth obtained by carrying out extraction on a raw material with a solvent to a specific fermentation and light irradiation procedure. Herein, the ferment may be a solution obtained by dissolving a solute in a solvent, or may be a solvent-free or substantially solvent-free concentrate. It should be noted that, if not particularly emphasized or marked as "unirradiated by light" or "unirradiated by red light", the term "ferment" used herein refers to a ferment irradiated by red light in the fermentation procedure. For example, the "ferment" and "ferment (irradiated by red light)" refer to a ferment that is fermented and irradiated by red light; and the "ferment (unirradiated by red light)" refers to a ferment that is fermented but is unirradiated by red light.

Herein, the term "noni fruit" usually refers to a fruit of plants. The fruit may be a fruit with or without peel, or a fruit that is dried or processed by other physical methods to facilitate handling. The other physical methods may comprise, for example, keeping as a whole, mincing, dicing, milling, grinding, other processing methods for altering the size and physical integrity of a raw material, or any combination thereof.

Herein, the term "yeast", "lactic acid bacteria", and "acetic acid bacteria" respectively refer to yeast strains, lactic acid bacteria strains and acetic acid bacteria strains that are commercially available (for example, those can be purchased from domestic or foreign depository institutions), or yeast strains, lactic acid bacteria strains and acetic acid bacteria strains that are isolated and purified from natural sources by microbial isolation methods commonly used in the art.

In some embodiments, the noni fruit ferment is prepared by (a) mixing glucose and noni fruit with water for extraction, to obtain a noni fruit broth, and (b) fermenting the noni fruit broth with a plurality of bacteria strains.

In the step (b), the bacteria strains comprise yeast, lactic acid bacteria, and acetic acid bacteria, and the noni fruit broth with the bacteria strains incubated is irradiated by a red light source. In some embodiments, the red light source has a wavelength of 620 nm to 750 nm.

In some embodiments, noni fruit is subsequently subjected to the step (a) comprising a heating procedure and a cooling procedure, and the step (b) comprising a fermentation and light irradiation procedure, to obtain a noni fruit ferment (irradiated by red light).

In some embodiments, noni fruit is subsequently subjected to the step (a) comprising a crushing procedure, a heating procedure, and a cooling procedure, and the step (b) comprising a fermentation and light irradiation procedure, to obtain a noni fruit ferment (irradiated by red light).

In some embodiments, noni fruit is subsequently subjected to the step (a) comprising a heating procedure and a cooling procedure, and the step (b) comprising a fermentation and light irradiation procedure and a filtering procedure, to obtain a noni fruit ferment (irradiated by red light).

In some embodiments, noni fruit is subsequently subjected to the step (a) comprising a heating procedure and a cooling procedure, and the step (b) comprising a fermentation and light irradiation procedure, a filtering procedure, and a concentration procedure, to obtain a noni fruit ferment (irradiated by red light).

In some embodiments, noni fruit is subsequently subjected to the step (a) comprising a crushing procedure, a heating procedure, and a cooling procedure, and the step (b) comprising a fermentation and light irradiation procedure and a filtering procedure, to obtain a noni fruit ferment (irradiated by red light).

In some embodiments, noni fruit is subsequently subjected to the step (a) comprising a crushing procedure, a heating procedure, and a cooling procedure, and the step (b) comprising a fermentation and light irradiation procedure, a filtering procedure, and a concentration procedure, to obtain a noni fruit ferment (irradiated by red light).

In some embodiments, the noni fruit may be noni fruit with or without peel. In some embodiments, the noni fruit may be fresh or dry noni fruit.

In some embodiments, the crushing procedure refers to whipping the noni fruit into noni fruit pieces. For example, the noni fruit pieces may be obtained through whipping by using a juicer, a food processor, or a homogenizer.

In some embodiments, in the heating procedure, the noni fruit and water are first mixed to obtain an initial broth; the initial broth is then subjected to extraction (digestion) at 95±5° C. for 1±0.5 hours to obtain an aqueous noni fruit extract; and glucose is then added into the aqueous noni fruit extract to obtain a noni fruit broth. It should be noted that, in the heating procedure, if the amount of a solvent (such as water) used is excessively small, or the time of extraction (digestion) is excessively short, the extraction (digestion) efficiency will decrease significantly; and if the time of extraction (digestion) is excessively long, active ingredients in the noni fruit broth may be degraded.

In some embodiments, in the heating procedure, glucose and noni fruit are first mixed with water to form an initial broth; and the initial broth is then subjected to extraction (digestion) at 95±5° C. for 1±0.5 hours to obtain a noni fruit broth. The glucose and noni fruit are added at the same time for mixing and extraction (digestion), so that it is not necessary to start an extraction (digestion) equipment for addition of the glucose. The added glucose may be further processed at a high temperature, which helps to dissolve the glucose and reduces the risk of contamination of the raw material.

In some embodiments, in the heating procedure, a weight ratio (a liquid-solid ratio) of water to noni fruit is 3:1 to 5:1 (that is, the water is 3 folds to 5 folds of the noni fruit by weight).

In some embodiments, in the heating procedure, the glucose is added in an amount of 5±3 wt % of a total weight of the water and the noni fruit. The addition of glucose can allow the noni fruit broth to have sufficient sugar content to ensure that bacteria strains used in fermentation can have sufficient nutrients, so that the subsequent fermentation and light irradiation procedure can be carried out smoothly.

In some embodiments, the cooling procedure refers to cooling the heated initial broth down to a specific temperature range. For example, the specific temperature range is below 38±3° C.

In some embodiments, before the fermentation and light irradiation procedure, solid substances (such as the extracted/digested noni fruit) are not filtered out of the noni fruit broth, and active ingredients are further extracted from the solid substances with the bacteria strains used in the fermentation and light irradiation procedure. In some embodiments, before the fermentation and light irradiation procedure, solid substances are first filtered out of the noni fruit broth, so that other complex and undesired ingredients can be avoided in the subsequent fermentation and light irradiation procedure, to better control the quality of the noni fruit ferment.

In some embodiments, the fermentation and light irradiation procedure refers to incubating a plurality of bacteria strains (comprising yeast, lactic acid bacteria, and acetic acid bacteria) into the noni fruit broth at once or in multiple stages for fermentation. During the fermentation, the noni fruit broth with bacteria strains incubated is irradiated by a red light source in the entire fermentation and light irradiation procedure to obtain a noni fruit ferment (irradiated by red light). In some embodiments, the red light source has a wavelength of 620 nm to 720 nm. For example, the red light source is a red LED light source with a wavelength of about 635 nm. The noni fruit broth with bacteria strains incubated is irradiated by a red light source, so that the growth rate of the bacteria strains can be increased, and the content of active ingredients in the noni fruit ferment can be further increased.

In some embodiments, the yeast used in the fermentation and light irradiation procedure is commercially available *Saccharomyces cerevisiae*. For example, the yeast used may be *Saccharomyces cerevisiae* with a deposit number BCRC20271 (an international deposit number ATCC26602) purchased from the Food Industry Research and Development Institute.

In some embodiments, the lactic acid bacteria used in the fermentation and light irradiation procedure is commercially available *Lactobacillus helveticus, Lactobacillus plantarum, Streptococcus thermophilus,* or *Lactiplantibacillus plantarum.* For example, the lactic acid bacteria may be *Lactobacillus plantarum* TCI378 with a deposit number BCRT910760 (an international deposit number DSM32451).

In some embodiments, the acetic acid bacteria used in the fermentation and light irradiation procedure may be acetic acid bacteria with a deposit number BCRC11688 (an international deposit number ATCC15973) purchased from the American Type Culture Collection.

In some embodiments, in the fermentation and light irradiation procedure, relative to the noni fruit broth, the used bacteria strains comprise 0.01 wt % to 0.5 wt % of yeast, 0.01 wt % to 0.25 wt % of lactic acid bacteria, and 1 wt % to 20 wt % of acetic acid bacteria.

In some embodiments, in the fermentation and light irradiation procedure, a plurality of bacteria strains (comprising yeast, lactic acid bacteria, and acetic acid bacteria) are incubated at once or in multiple stages to ferment for about 3 days to 16 days (that is, 72 hours to 384 hours). In some embodiments, a fermentation time for the yeast may be 1 day to 3 days (that is, 24 hours to 72 hours), a fermentation time for the lactic acid bacteria may be 1 day to 3 days (that is, 24 hours to 72 hours), and a fermentation time for the acetic acid bacteria may be 3 days to 10 days (that is, 72 hours to 240 hours).

In some embodiments, in the fermentation and light irradiation procedure, a plurality of bacteria strains (comprising yeast, lactic acid bacteria, and acetic acid bacteria) are incubated in three stages for fermentation. For example, in the fermentation and light irradiation procedure, the yeast is first incubated into the noni fruit broth to convert the sugar (for example, glucose) in the noni fruit broth into ethanol through fermentation. The ethanol helps extract active ingredients from the noni fruit broth to form a first initial ferment. Then, the lactic acid bacteria are incubated into the first initial ferment to form a second initial ferment. The incubation of the lactic acid bacteria into the first initial ferment can allow the unreacted sugar in the first initial ferment to be converted into lactic acid through fermentation to further consume the sugar therein, so as to reduce the sugar content of the second initial ferment. The lactic acid produced from the second initial ferment will further change the overall reaction environment (for example, reduce the pH value of the second initial ferment), which will also affect and help the extraction of active ingredients from the noni fruit broth (allowing the active ingredients dissolved in the acid solution easier to be extracted). Then, the acetic acid bacteria are incubated into the second initial ferment to form a noni fruit ferment. Based on this, the ethanol in the second initial ferment may be converted into acetic acid. The ethanol is further consumed, so that the yeast can further convert the sugar into ethanol to make the reaction with the yeast more complete and further reduce the sugar content. In some embodiments, the Brix degree of the noni fruit ferment is 23° Bx to 27° Bx to ensure the complete fermentation reaction. In some embodiments, the pH value of the noni fruit ferment is about 2.3 to 4.3.

In some embodiments, in the fermentation and light irradiation procedure, a plurality of bacteria strains (comprising yeast, lactic acid bacteria, and acetic acid bacteria) are incubated in three stages for fermentation. For example, in the fermentation and light irradiation procedure, the yeast and the lactic acid bacteria used are incubated in any order to form the first initial ferment; and the acetic acid bacteria is finally incubated into the first initial ferment for fermentation to form the second initial ferment. Therefore, it can be ensured that ethanol has been produced in the first initial ferment to allow the acetic acid bacteria to grow better and to convert the ethanol, so as to reduce the content of ethanol in the second initial ferment. In some embodiments, a fermentation time for the acetic acid bacteria is longer than a fermentation time for the yeast, and the fermentation time for the acetic acid bacteria is also longer than a fermentation time for the lactic acid bacteria, so that the acetic acid bacteria can consume ethanol completely in the second initial ferment.

In some embodiments, in the fermentation and light irradiation procedure, a plurality of bacteria strains (comprising yeast, lactic acid bacteria, and acetic acid bacteria) are incubated in two stages for fermentation. For example, the yeast and the lactic acid bacteria may be first incubated into the noni fruit broth simultaneously for fermentation to form a first initial ferment. Then, the acetic acid bacteria are incubated into the first initial ferment for fermentation to form a noni fruit ferment. The yeast and the lactic acid bacteria react rapidly and require a similar fermentation time, so that the incubation of the acetic acid bacteria after the yeast and the lactic acid bacteria can allow the noni fruit broth to complete the fermentation reaction for the first initial ferment at the stage of fermentation with the yeast and the lactic acid bacteria for a short time (for example, co-fermentation for 1 day), so as to reduce a total time required for the fermentation for the noni fruit ferment.

In some embodiments, the yeast, the lactic acid bacteria, and the acetic acid bacteria used in the fermentation and light irradiation procedure may react for fermentation at 25° C. to 40° C., preferably 28° C. to 32° C. If the temperature exceeds 40° C., the bacteria strains will be inactivated; and if the temperature is lower than 25° C., the fermentation reaction will have an excessively low rate or even cannot be carried out. These cases are not helpful in obtaining a first initial ferment, a second initial ferment, and/or a noni fruit ferment.

In some embodiments, the filtering procedure refers to filtering out solid substances from the noni fruit ferment after the fermentation and light irradiation procedure with a filter to form a noni fruit ferment (filtrate). For example, the filter may be a 200-mesh filter.

In some embodiments, the concentration procedure refers to concentrating the noni fruit ferment after the fermentation and light irradiation procedure under reduced pressure (by using an evaporator with a brand/model: BUCHI-Rotavapor R-100), or concentrating the noni fruit ferment (filtrate) after the filtering procedure (by using an evaporator with a brand/model: BUCHI-Rotavapor R-100), to adjust the concentration of ingredients of the noni fruit ferment to obtain a noni fruit ferment (concentrate).

In some embodiments, oligosaccharide may be added into the noni fruit ferment (filtrate)/the noni fruit ferment (concentrate)/the noni fruit ferment to obtain a desired sugar content of the finally-obtained noni fruit ferment. In some embodiments, the oligosaccharide is a polymer containing 3 to 10 monosaccharides. In some embodiments, the oligosaccharide may be fructooligosaccharide, galacto-oligosaccharide, xylooligosaccharide, or isomalto-oligosaccharide. For example, the isomalto-oligosaccharide of 40 wt % to 70 wt % (preferably 60 wt %), relative to a weight of the noni fruit ferment (filtrate)/the noni fruit ferment (concentrate)/the noni fruit ferment, may be added into the noni fruit ferment (filtrate)/the noni fruit ferment (concentrate)/the noni fruit ferment to obtain a Brix degree of 23° Bx to 27° Bx and a pH value of 2.7 to 3.7 of the finally-obtained noni fruit ferment.

In some embodiments, the noni fruit ferment can be used for improving body shape. The noni fruit ferment contributes to the improving body shape (comprising at least one of increasing whole body muscle mass, reducing whole body fat percentage, reducing belly fat mass and/or leg fat mass, reducing subcutaneous fat mass and/or visceral fat mass, and reducing waist circumference) by promoting leptin production and/or promoting fat metabolism.

In some embodiments, the noni fruit ferment contributes to the promoting fat metabolism by increasing an expression level of one or more fat loss genes. In some embodiments, the one or more fat loss genes may be at least one of adipose triglyceride lipase (ATGL) gene, lipase E (LIPE) gene, and uncoupling protein 1 (UCP1) gene.

In some embodiments, the noni fruit ferment can be used for improving skin condition. The improving skin condition may be at least one of reducing skin redness, improving skin elasticity, and reducing sun spots.

In some embodiments, the noni fruit ferment contributes to the improving skin elasticity by promoting elastin production.

In some embodiments, the noni fruit ferment further has at least one of the following functions: anti-oxidation and removing surface free radicals.

In some embodiments, the noni fruit ferment further has at least one of the following functions: improving defecation status and improving gastrointestinal motility.

In the following examples, statistical analysis was conducted by using Excel software. Data was expressed as mean±standard deviation (SD), and the differences between groups were analyzed by student's 1-test. In addition, in the corresponding figures, "*" represented a p-value less than 0.05, "" represented a p value less than 0.01, and "*" represented a p value less than 0.001. More "*" represented more significant statistical differences.

Example 1: Preparation Method of Noni Fruit Ferment

The steps of the preparation method were shown as follows:
1. First, noni fruit was coarsely crushed (with a 10-speed blender of brand Osterizer), and sieved with a sieve with a pore size of 12 mm to remove large particles, to obtain the crushed noni fruit.
2. Then, water and the crushed noni fruit were mixed in a liquid-solid weight ratio of 3:1, and glucose of 5 wt % was added relative to a total weight of the water and the crushed noni fruit, to form a liquid mixture. The liquid mixture was subjected to extraction (digestion) at 95° C. for 1 hour to obtain a noni fruit broth.
3. The noni fruit broth was then cooled down to below 38° C.
4. Then, the noni fruit broth was irradiated by a red LED light source at a wavelength of 635 nm in the entire step 4. 0.1 wt % of *Saccharomyces cerevisiae* (deposit number BCRC20271) was incubated into the noni fruit broth to ferment for 1 day, then 0.05 wt % of *Lactobacillus plantarum* TCI378 (international deposit number DSM32451, deposit number BCRT910760) was incubated to ferment for 1 day, and then 5 wt % of *Acetobacter aceti* (deposit number BCRC11688) was incubated to ferment for 5 days, to obtain a noni fruit ferment.
5. Then, the noni fruit ferment was filtered with a 200-mesh filter to obtain a noni fruit ferment (filtrate).
6. The noni fruit ferment (filtrate) was concentrated under reduced pressure at 55° C. to 65° C., and at the same time, 60 wt % of isomalto-oligosaccharide was added, to obtain a noni fruit ferment (concentrate). The concentration was carried on until the noni fruit ferment (concentrate) had a Brix degree of 2512° Bx and a pH value of 3.2±0.5.
7. Then, the noni fruit ferment (concentrate) was sterilized at 100° C. for 2 hours to obtain a final noni fruit ferment.

It should be noted that the noni fruit ferment (unirradiated by red light) used in the following experimental detection was prepared by the method in Example 1. The difference was that, in the step 4 of the preparation method in Example 1, the noni fruit ferment (unirradiated by red light) was irradiated by natural light instead of the red LED light source. The rest of the irradiation time and conditions were the same as those of the noni fruit ferment (irradiated by red light).

In addition, the noni fruit broth used in the following experimental detection was prepared by the method in Example 1. The difference was that the noni fruit broth did not undergo the step 4 of the preparation method in Example 1. The rest of the conditions were the same as those of the noni fruit ferment (irradiated by red light).

Example 2: Quantification of Polyphenols of Noni Fruit Ferment

A standard curve was drawn as follows:
First, 10 mg of gallic acid (GA, purchased from Sigma, product number: G7384) was dissolved in water to obtain a solution, and 10 mL of the solution was added into a volumetric flask to obtain a 1000 μg/mL GA solution (that is, 1000 ppm GA), and then the solution was stored at −20° C. as a stock solution. Next, the stock solution was diluted 10-fold to a concentration of 100 μg/mL, and the unused solution was stored at −20° C. Then, 0 μg/mL, 20 μg/mL, 40 μg/mL, 60 μg/mL, 80 μg/mL, and 100 μg/mL GA standard solutions were respectively prepared in glass test tubes with preparation formulas shown in the following Table 1:

TABLE 1

| Preparation formula of GA standard solution | | | | | | |
|---|---|---|---|---|---|---|
| | Concentration (μg/mL) | | | | | |
| | 0 | 20 | 40 | 60 | 80 | 100 |
| GA 1,000 ppm | 0 μL | 20 μL | 40 μL | 60 μL | 80 μL | 100 μL |
| ddH$_2$O | 100 μL | 80 μL | 60 μL | 40 μL | 20 μL | 0 μL |

500 μL of Folin-Ciocalteu's phenol reagent (purchased from Merck, product number: 1.09001.0100) was then added and mixed uniformly to stand for 3 min, and then 400 μL of 7.5% sodium carbonate (dissolved in water, Sigma 31432) was added and mixed uniformly to react for 30 min. Then, 200 μL of standard solution was taken after it was ensured that there were no air bubbles through vortex to measure an absorbance at 750 nm, and a standard curve was drawn.

Experiment of Quantification of Total Polyphenols in Samples:

A control group 1 (noni fruit broth), a control group 2 (noni fruit ferment (unirradiated by red light)), and an experimental group (noni fruit ferment (irradiated by red light)) that were obtained by the preparation method in the Example 1 were used as samples. Each group was diluted 20-fold with water to 1200 μL and 100 μL of the solution was taken into a glass test tube. This operation in each group required to be repeated three times. Then, 500 μL of Folin-Ciocalteu's phenol reagent was added and mixed uniformly to stand for 3 min.

400 μL of 7.5% sodium carbonate was then added and mixed uniformly to react for 30 min to 1 hour. 200 μL of reaction solution in each group was taken after it was ensured that there were no air bubbles through vortex to measure an absorbance at 750 nm, a concentration was calculated by interpolation, and then the concentration was multiplied by a dilution factor to obtain an original concentration.

Referring to FIG. 1, as compared with the control group 1 and the control group 2, the total content of polyphenols in the experimental group was significantly increased. As compared with the control group 1, the total content of polyphenols in the experimental group was increased by about 2.49 folds. As compared with the control group 2, the total content of polyphenols in the experimental group was increased by about 1.26 folds. Therefore, the experimental results in FIG. 1 show that the noni fruit ferment irradiated by red light released a large amount of polyphenols, which effectively changed the ingredients contained in the noni fruit ferment, and effectively increased the active ingredients. The noni fruit ferment (irradiated by red light) was proven to have functions of removing free radicals and anti-oxidation due to the capability of polyphenols in removing free radicals and anti-oxidation, and the noni fruit ferment (irradiated by red light) showed better capability in removing free radicals and anti-oxidation than the noni fruit ferment (unirradiated by red light).

Example 3: Cell Experiment—Increasing Leptin

A cell differentiation medium used herein was a DMEM medium supplemented with 10 vol % of FBS (brand: Gibco, number 10437-028), 1 vol % of antibiotic-antimycotic (AA, Gibco, product number: 15240-062), 1.0 μM/mL of dexamethasone (DEXA; brand: Sigma, number 50-02-2), 0.5 mM/mL of methylisobutylxanthine (IBMX; brand: Sigma, number 28822-58-4), and 1.0 μg/mL of insulin (brand: Sigma, number 19278). A fat maintenance medium used herein was a DMEM medium (brand: Gibco) supplemented with 10 vol % of FBS, 1 vol % of AA, and 1.0 μg/mL of insulin.

Detection Process:

First, 3T3-L1 cells (purchased from BCRC, number 60159) were inoculated into a 96-well culture plate containing 100 μL of cell differentiation medium per well in a density of $1\times10^4$ cells per well, and then cultured at 37° C. for 6 days. During the 6-day culture, the cell differentiation medium was replaced with a fresh one every two days. Then, after the 6-day culture, the cell differentiation medium was replaced with a fat maintenance medium, and then cultured at 37° C. for 7 days. During the 7-day culture, the fat maintenance medium was replaced with a fresh one every two days. After the 7-day culture, the formation of lipid droplets in cells in each well was observed by using a microscope (brand: ZEISS) to confirm that the cells were fully differentiated into fat cells for subsequent experiments.

The fat cells were divided into four groups: an experimental group, a control group 1, a control group 2, and a blank group. The differentiation medium in each group was replaced with 100 μL of experimental medium per well, and then cultured at 37° C. for 12 days. During the 12-day culture, the experimental medium was replaced with a fresh one every two days. In a first experiment (corresponding to experimental results shown in FIG. 2), the experimental medium in the experimental group contained 0.125 vol % of the noni fruit ferment (irradiated by red light) prepared by the method in the Example 1; the experimental medium in the control group 1 contained 0.125 vol % of the noni fruit broth prepared by the method in the Example 1; the experimental medium in the control group 2 contained 0.125 vol % of the noni fruit ferment (unirradiated by red light) prepared by the method in the Example 1; and the experimental medium in the blank group did not contain the noni fruit broth, the noni fruit ferment (unirradiated by red light), and the noni fruit ferment (irradiated by red light). In a second experiment (corresponding to experimental results shown in FIG. 3), the experimental medium in the experimental group contained 0.25 vol % of the noni fruit ferment (irradiated by red light) prepared by the method in the Example 1; the experimental medium in the control group 1 contained 0.25 vol % of the noni fruit broth prepared by the method in the Example 1; the experimental medium in the control group 2 contained 0.25 vol % of the noni fruit ferment (unirradiated by red light) prepared by the method in the Example 1; and the experimental medium in the blank group did not contain the noni fruit broth, the noni fruit ferment (unirradiated by red light), and the noni fruit ferment (irradiated by red light).

Then, the culture medium of 3T3-L1 cells in each group was collected and the content of leptin in each group was detected by using a Mouse LEP (Leptin) ELISA kit (brand: Elabscience, number E-EL-M3008).

Herein, a relative yield of leptin detected from the blank group was regarded as 100% to calculate relative yields of leptin of the control group 1, the control group 2, and the experimental group. In addition, as shown in FIG. 2 and FIG. 3, the statistical significance difference between groups was counted and analyzed through the student's t-test.

Figure 2:
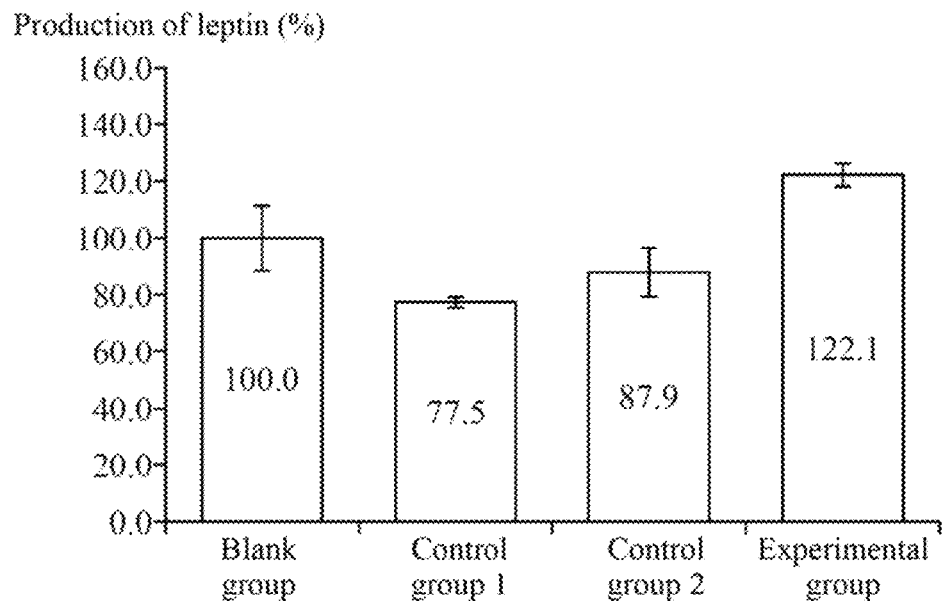
FIG. 2 and FIG. 3 are diagrams showing detection results of leptin production of a noni fruit ferment prepared by the method in Example 1 and other control groups.

In FIG. 2, except for the blank group, the experimental medium in other groups contained 0.125 vol % of the foregoing to-be-detected samples. As shown in FIG. 2, the relative production of leptin in the experimental group was 122.1%, while the relative production of leptin in the control group 1 was 77.5%, and the relative production of leptin in the control group 2 was 87.9%. In other words, the relative production of leptin in the experimental group was significantly higher than those in the control group 1 and control group 2. The noni fruit ferment (irradiated by red light) was proven to effectively promote leptin production of a subject, which in turn showed the capability in inhibiting the appetite of the subject and increasing the energy consumption of the subject.

Figure 3:
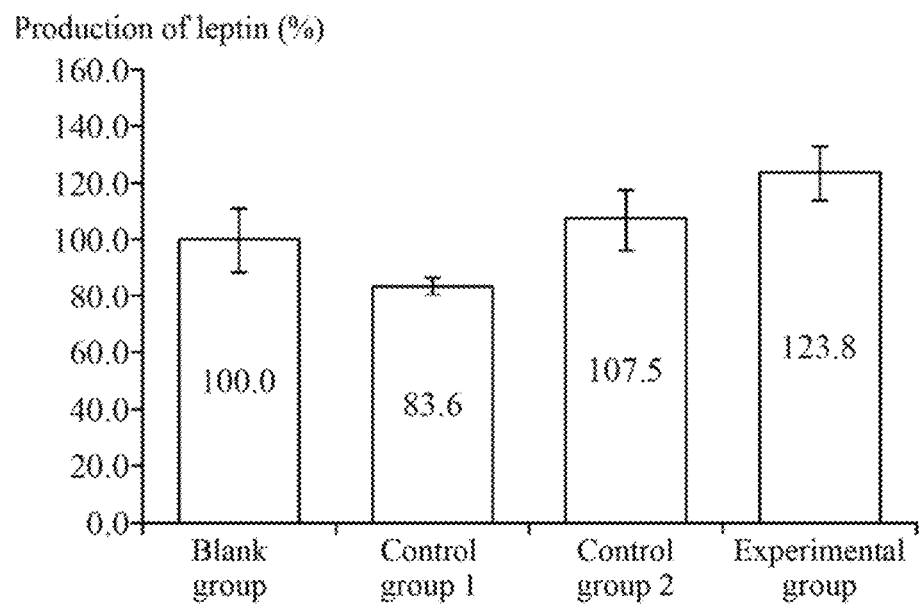

In addition, in FIG. 3, except for the blank group, the experimental medium in other groups contained 0.25 vol % of the foregoing to-be-detected samples. As shown in FIG. 3, the relative production of leptin in the experimental group was 123.8%, while the relative production of leptin in the control group 1 was 83.6%, and the relative production of leptin in the control group 2 was 107.5%. In other words, the relative production of leptin in the experimental group was significantly higher than those in the control group 1 and control group 2. The noni fruit ferment (irradiated by red light) was proven to effectively promote leptin production of a subject, which in turn showed the capability in inhibiting the appetite of the subject and increasing the energy consumption of the subject.

By combining the experimental results of FIG. 2 and FIG. 3, the noni fruit ferment (irradiated by red light) was proven to effectively promote leptin production of a subject, which in turn showed the capability in inhibiting the appetite of the subject, increasing the energy consumption of the subject, and improving body shape.

Example 4: Cell Experiment—Promoting Fat Metabolism and Increasing Expression Level of Fat Metabolism Genes Material and Instrument:

Cell strain: mouse bone marrow stromal cells OP9 (purchased from BCRC, number 6566).

Culture medium: α-minimum essential medium (α-MEM, Gibco, number 12000-022) containing 20% of fetal bovine serum (FBS, Gibco, number 10438-026, USA) and 1% of antibiotic-antimycotic (Gibco, number 15240-062).

RNA extraction reagent kit (purchased from Geneaid, Taiwan, Lot No. FC24015-G).

SuperScript® III Reverse Transcriptase (Invitrogen, USA, number 18080-051).

Measurement target gene primers, comprising ATGL genes, LIPE (HSL) genes, and UCP1 genes, and also comprising an internal control group (m-ACTB genes).

KAPA SYBR® FAST qPCR reagent kit (purchased from Sigma, USA, number 38220000000).

ABI StepOnePlus™ Real-Time PCR system (Thermo Fisher Scientific, USA).

Experimental samples: the noni fruit broth, the noni fruit ferment (unirradiated by red light), and the noni fruit ferment (irradiated by red light) that were obtained by the preparation method in the Example 1.

Experimental Steps:

First, $1.5 \times 10^5$ mouse bone marrow stromal cells were inoculated into a cell culture plate containing 2 mL of the foregoing culture medium per well, and then cultured at 37° C. for 24 hours, and the cultured mouse bone marrow stromal cells were divided into four groups: a blank group, a control group 1 (noni fruit broth), a control group 2 (noni fruit ferment (unirradiated by red light)), and an experimental group (noni fruit ferment (irradiated by red light)) according to the following Table 2. The culture medium in each group was replaced with 2 mL of experimental medium, and then cultured for 24 hours. Each group was repeated for three times.

TABLE 2

| | Test condition | |
|---|---|---|
| | Experimental medium | |
| Group | Added component | Addition concentration |
| Group A (Blank group) | None | None |
| Group B (Control group 1) | Noni fruit broth | 0.025 mg/mL |
| Group C (Control group 2) | Noni fruit ferment (unirradiated by red light) | 0.025 mg/mL |
| Group D (Experimental group) | Noni fruit ferment (irradiated by red light) | 0.025 mg/mL |

The cell membranes of the treated mouse bone marrow stromal cells (in the groups B to D) and the untreated mouse bone marrow stromal cells in the blank group (the group A) were broken with a cell lysis buffer to form four groups of cell solutions. Next, RNA of the four groups of cell solutions was extracted separately by using an RNA extraction reagent kit (purchased from Geneaid, Taiwan, Lot No. FC24015-G). Then, 1000 ng of the extracted RNA in each group was used as a template, and the extracted RNA was reverse transcribed into corresponding cDNA by the SuperScripe III reverse transcriptase (purchased from Invitrogene, USA, number 18080-051). Subsequently, the quantitative real-time reverse transcription polymerase chain reaction was carried out on the four groups of cDNA with the primers (SEQ ID NO: 1 to SEQ ID NO: 8) in Table 3 by using the ABI StepOnePlus™ Real-Time PCR system (Thermo Fisher Scientific, USA) and the KAPA SYBR FAST (purchased from Sigma, USA, number 38220000000) to observe the expression level of ATGL genes, LIPE (HSL) genes, and UCP1 genes of the mouse bone marrow stromal cells in the four groups. The instrument setting conditions for the quantitative real-time reverse transcription polymerase chain reaction were 95° C. for 20 sec, 95° C. for 3 sec, 60° C. for 30 sec, a total of 40 cycles, and gene quantification was carried out by the $2^{-\Delta Ct}$ method. Herein, the quantitative real-time reverse transcription polymerase chain reaction with cDNA indirectly quantified the mRNA expression level of the ATGL genes, the LIPE (HSL) genes, and the UCP1 genes, and then inferred the expression level of the protein encoded by the ATGL genes, the LIPE (HSL) genes, and the UCP1 genes.

TABLE 3

| Gene | Primer name | Sequence NO. | Primer sequence |
|---|---|---|---|
| ATGL | ATGL-F | SEQ ID NO: 1 | GGATGGCGGCATTTCAGACA |
|  | ATGL-R | SEQ ID NO: 2 | CAAAGGGTTGGGTTGGTTCAG |
| LIPE | LIPE-F | SEQ ID NO: 3 | TGGCACACCATTTTGACCTG |
|  | LIPE-R | SEQ ID NO: 4 | TTGCGGTTAGAAGCCACATAG |
| UCP1 | UCP1-F | SEQ ID NO: 5 | AGGCTTCCAGTACCATTAGGT |
|  | UCP1-R | SEQ ID NO: 6 | CTGAGTGAGGCAAAGCTGATTT |
| β-actin | ACTB-F | SEQ ID NO: 7 | GGCTGTATTCCCCTCCATCG |
|  | ACTB-R | SEQ ID NO: 8 | CCAGTTGGTAACAATGCCATGT |

*R is REVERSE, and F is FORWARD.

Figure 4:
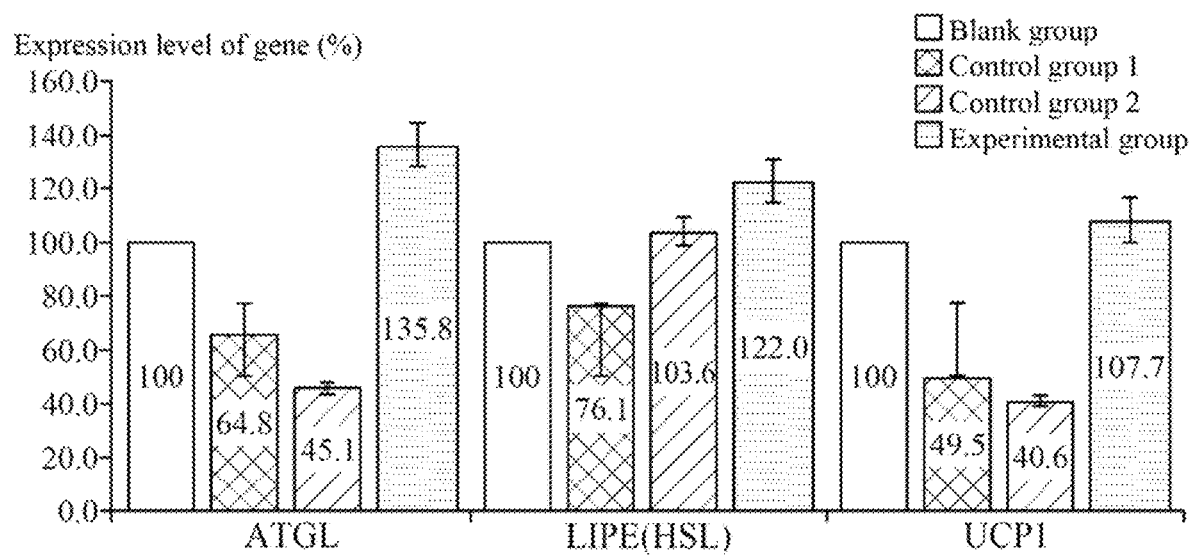
FIG. 4 is a diagram showing detection results of expression levels of fat loss genes of a noni fruit ferment prepared by the method in Example 1 and other control groups.

Noted that the relative gene expression levels of the ATGL genes, the LIPE (HSL) genes, and the UCP1 genes shown in FIG. 4 were presented by relative magnification. The standard deviation was calculated by using the STDEV formula of Excel software, and whether there was a statistically significant difference was analyzed by one-tailed student's t-test in Excel software.

As shown in FIG. 4, when the expression levels of the ATGL genes, the LIPE (HSL) genes, and the UCP1 genes in the blank group (group A) were respectively regarded as 1 (that is, 100%), for the experimental group (group D), the expression level of the ATGL genes relative to the group A was about 135.8%, the expression level of the LIPE (HSL) genes relative to the group A was about 122.0%, and the expression level of the UCP1 genes relative to the group A was about 107.7%, indicating that, for the experimental group (group D), the expression level of the ATGL genes was increased 1.358 folds of that of the group A, the expression level of the LIPE (HSL) genes was increased 1.22 folds of that of the group A, and the expression level of the UCP1 genes was increased 1.077 folds of that of the group A. Results showed that, after the mouse bone marrow stromal cells were treated with 0.025 mg/mL of noni fruit ferment (irradiated by red light), the expression levels of the ATGL genes, the LIPE (HSL) genes, and the UCP1 genes of the mouse bone marrow stromal cells were increased.

Then, the experimental group (group D) was compared with the control group 1 (group B) and the control group 2 (group C). The expression level of the ATGL genes in the experimental group was higher than those in the group B and the group C, respectively, 2.10 folds of that of the group B and 3.01 folds of that of the group C. The expression level of the LIPE (HSL) genes in the experimental group was higher than those in the group B and the group C, respectively, 1.60 folds of that of the group B and 1.18 folds of that of the group C. The expression level of the UCP1 genes in the experimental group was higher than those in the group B and the group C, respectively, 2.18 folds that of the group B and 2.65 folds that of the group C.

The protein encoded by the ATGL gene is ATGL. A triglyceride is a main component of lipid droplets of fat cells or fat tissues, and also a main source of stored energy in fat cells. The main function of ATGL is to decompose triglycerides. The ATGL exists on the surface of lipid droplets, and can decompose triglycerides when activated to provide energy for individuals. Therefore, the increased expression level of ATGL genes would promote the decomposition of fat in fat cells, and reduce the accumulation amount of fat in fat cells. Therefore, as shown by the experimental results in FIG. 4, the noni fruit ferment (irradiated by red light) was proven to significantly increase the expression level of ATGL genes (that is, genes related to fat metabolism (fat loss)), so that the noni fruit ferment (irradiated by red light) showed the capability in improving the activity of fat metabolism, and then promoting fat decomposition, thereby preventing and reducing obesity symptoms more effectively.

The protein encoded by the LIPE gene is a lipase with a long form and a short form. The long-form lipase is mainly expressed in steroidogenic tissues (such as testis), and has a main function of converting cholesteryl esters into free cholesterol for subsequent production of steroid hormones. The short-form lipase is mainly expressed in fat tissues, and has a main function of hydrolyzing stored triglycerides into free fatty acids. Therefore, the increased expression level of LIPE genes promotes the decomposition of fat in fat cells, and reduces the accumulation amount of fat in fat cells. In addition, the ATGL gene and the LIPE gene respectively transcribe ATGL and hormone-sensitive lipase (HSL). Specifically, ATGL can hydrolyze triglycerides stored in cells into free fatty acids and diglycerides, and HSL further hydrolyzes the diglycerides into monoglycerides, both of which play a pivotal role in fat loss. Therefore, as shown by the experimental results in FIG. 4, the noni fruit ferment (irradiated by red light) was proven to significantly increase the expression level of LIPE (HSL) genes (that is, genes related to fat metabolism (fat loss)), so that the noni fruit ferment (irradiated by red light) showed the capability in improving the activity of fat metabolism, and then promoting fat decomposition, thereby preventing and reducing obesity symptoms more effectively.

The protein encoded by the UCP1 gene is UCP, which is one of the mitochondrial anion carrier proteins (MACPs), and has main functions of reducing adenosine triphosphate (ATP), promoting the transfer of anions from the inner membrane of mitochondria to the outside and promoting the return transfer of protons from the outside to the inner membrane of mitochondria, and releasing the energy generated in the process as thermal energy. The UCP1 gene is only expressed in brown fat cells, and the brown fat cells contain a large amount of mitochondria, which can burn lipid droplets to generate thermal energy. Therefore, the increased expression level of UCP1 genes promotes the decomposition of fat, and reduces the accumulation amount of fat. Hence, as shown by the experimental results in FIG. 4, the noni fruit ferment (irradiated by red light) was proven to significantly increase the expression level of the UCP1 genes (that is, genes related to fat metabolism (fat loss)), so that the noni fruit ferment (irradiated by red light) showed the capability in improving the activity of fat metabolism, and then promoting fat decomposition, thereby preventing and reducing obesity symptoms more effectively.

From above, as shown by the experimental results in FIG. 4, the noni fruit ferment (irradiated by red light) was proven to significantly increase the expression level of at least one of three genes related to fat metabolism (fat loss) of ATGL genes, LIPE (HSL) genes, and UCP1 genes, so that the noni fruit ferment (irradiated by red light) showed the capability in improving the activity of fat metabolism, and then promoting fat decomposition, thereby preventing and reducing obesity symptoms more effectively. In addition, as shown by the experimental results in FIG. 4, the noni fruit ferment (irradiated by red light) showed better performance in improving the activity of fat metabolism, promoting fat decomposition, and preventing and reducing obesity symptoms than the noni fruit broth and the noni fruit ferment (unirradiated by red light).

Example 5: Cell Experiment—Promoting Elastin Production

A culture medium used herein was a cell medium (referred to as an MEM medium below) containing 90 vol % of minimum essential medium (brand: Gibco), 10 vol % of fetal bovine serum (FBS; brand: Gibco), and 1 mM sodium pyruvate (brand: Gibco). A cell strain used herein was normal human dermal fibroblasts (CCD-966Sk cells, brand: ATCC®, CRL-1881).

The CCD-966Sk cells were inoculated in a culture plate containing 2 mL of MEM medium per well in a density of $1 \times 10^5$ cells per well, and then cultured at 37° C. for 24 hours. The CCD-966Sk cells were divided into four groups: an experimental group, a control group 1, a control group 2, and a blank group. Then, the MEM medium was replaced with an experimental medium, and the experimental group, the control group 1, the control group 2, and the blank group were cultured at 37° C. for 24 hours. The experimental medium in the experimental group contained 0.25 vol % of the noni fruit ferment (irradiated by red light) prepared by the method in the Example 1; and the experimental medium in the control group 1 contained 0.25 vol % of the noni fruit broth prepared by the method in the Example 1. The experimental medium in the control group 2 contained the noni fruit ferment (unirradiated by red light) prepared by the method in the Example 1. The experimental medium in the blank group did not contain the noni fruit broth, the noni fruit ferment (unirradiated by red light), and the noni fruit ferment (irradiated by red light).

Figure 5:
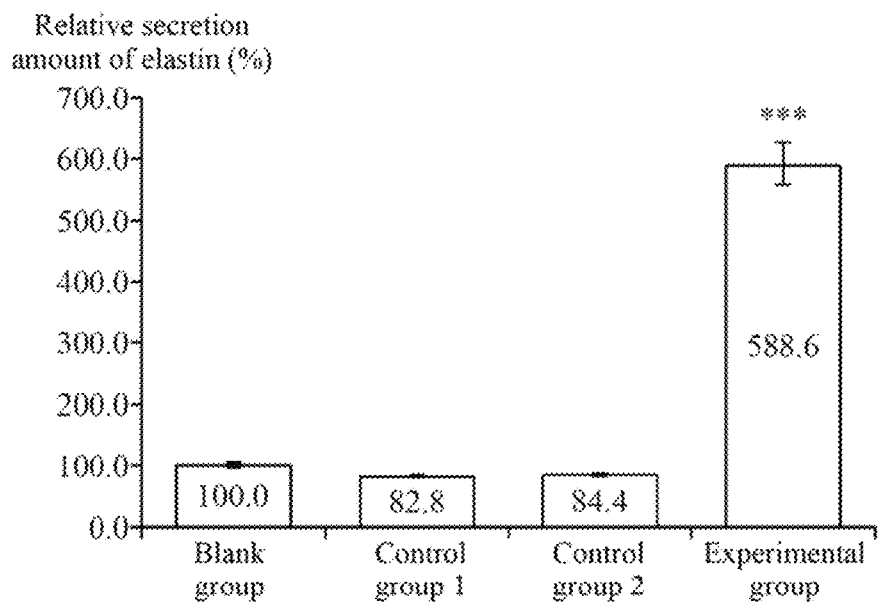
FIG. 5 is a diagram showing detection results of secretion amounts of elastin of a noni fruit ferment prepared by the method in Example 1 and other control groups.

Then, after the CCD-966Sk cells were treated by using the Fastin™ Elastin Assay kit (brand: Biocolor), the production of elastin of the CCD-966Sk cells in the four groups was detected by using a full spectrum optical analyzer (brand: BioTek, Epoch). The content of elastin measured from the blank group that was not cultured with the experimental medium for 24 hours was regarded as 1 (that is, the production of elastin was 100%). As shown in FIG. 5, the statistically significant difference between the groups was determined by student's t-test.

In FIG. 5, as compared with the blank group, the production of elastin in the experimental group was 588.6%, while the production of elastin in the control group 1 was 82.8%, and the production of elastin in the control group 2 was 84.4%. In other words, there was no significant difference in the production of elastin among the blank group, the control group 1, and the control group 2. As compared with the control group 1 and the control group 2, the production of elastin in the experimental group was significantly increased (respectively 7.10 folds of that in the control group 1 and 6.97 folds of that in the control group 2), indicating that, the CCD-966Sk cells cultured with the noni fruit ferment (irradiated by red light) was proven to produce more elastin. That is, the noni fruit ferment (irradiated by red light) showed the capability in promoting elastin synthesis in cells. Based on this, after a subject had taken the noni fruit ferment (irradiated by red light), the noni fruit ferment (irradiated by red light) in the subject was proven to promote skin cells of the subject to produce elastin to improve skin elasticity of the subject.

Example 6: Human Subject Experiment—Improving Body Shape

Eight obese subjects (with a body fat percentage greater than 25% or a BMI value greater than 24) were allowed to drink a 6 mL noni fruit fermented drink (containing 12 vol % of noni fruit ferment (irradiated by red light) prepared by the method in the Example 1) every day for two weeks. In addition, before taking (week 0) and after taking (week 2), weights of these subjects were measured with a scale, while belly and leg fat masses, whole body fat percentages, muscle masses, and subcutaneous and visceral fat masses of these subjects were measured with a body fat meter (brand: TANITA BC-601FS). Waist circumferences of these subjects were measured with a cloth ruler. As shown in FIG. 6 to FIG. 12, the statistical significance difference between measurement results at week 0 and week 2 was counted and analyzed through student's 1-test.

Figure 6:
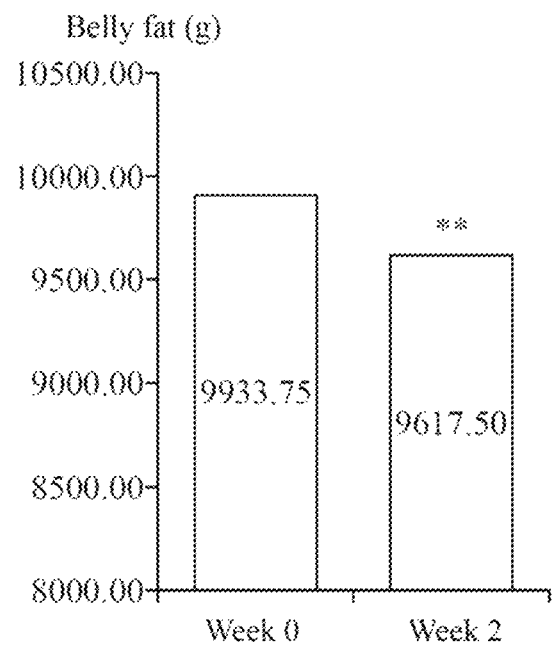
FIG. 6 is a diagram showing detection results of body fat mass (belly) before taking (week 0) and after taking (week 2) a noni fruit ferment prepared by the method in Example 1.

By the experimental results in FIG. 6, as compared with a fat mass (belly) before taking (week 0), the fat mass (belly) was reduced by about 316.25 g after taking the noni fruit fermented drink for two weeks.

Figure 7:
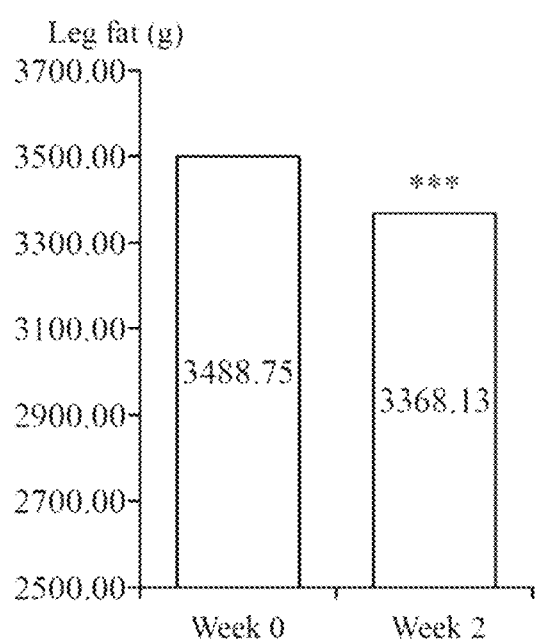
FIG. 7 is a diagram showing detection results of body fat mass (leg) before taking (week 0) and after taking (week 2) a noni fruit ferment prepared by the method in Example 1.

By the experimental results in FIG. 7, as compared with a fat mass (leg) before taking (week 0), the fat mass (leg) was reduced by about 120.62 g after taking the noni fruit fermented drink for two weeks.

Figure 8:
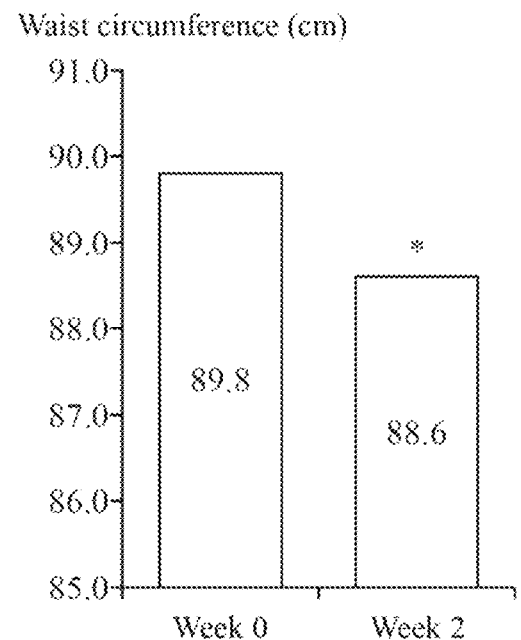
FIG. 8 is a diagram showing detection results of waist circumference before taking (week 0) and after taking (week 2) a noni fruit ferment prepared by the method in Example 1.

By the experimental results in FIG. 8, as compared with a waist circumference before taking (week 0), the waist circumference was reduced by about 1.2 cm after taking the noni fruit fermented drink for two weeks.

Figure 9:
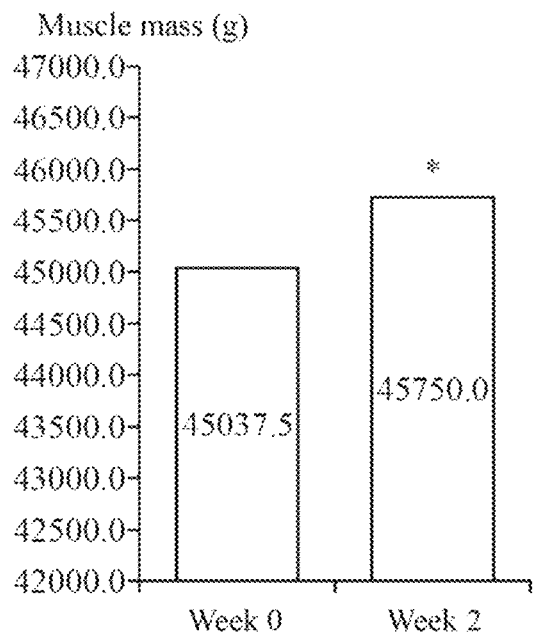
FIG. 9 is a diagram showing detection results of muscle mass before taking (week 0) and after taking (week 2) a noni fruit ferment prepared by the method in Example 1.

By the experimental results in FIG. 9, as compared with a muscle mass before taking (week 0), the muscle mass was increased by about 712.5 g after taking the noni fruit fermented drink for two weeks.

Figure 10:
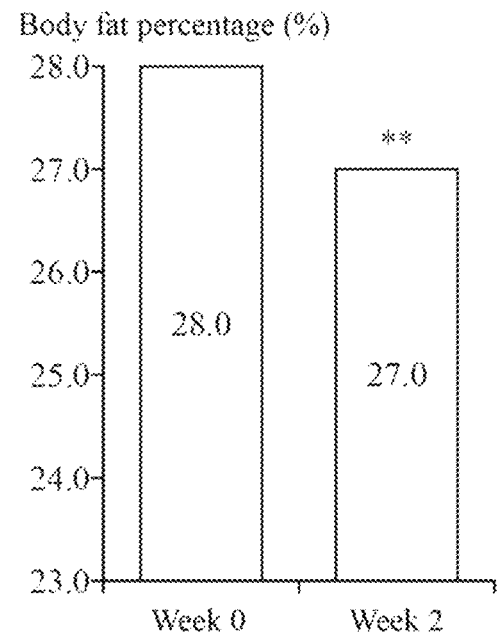
FIG. 10 is a diagram showing detection results of body fat percentage before taking (week 0) and after taking (week 2) a noni fruit ferment prepared by the method in Example 1.

By the experimental results in FIG. 10, as compared with a body fat percentage before taking (week 0), the body fat percentage was reduced by about 1.0% after taking the noni fruit fermented drink for two weeks.

Figure 11:
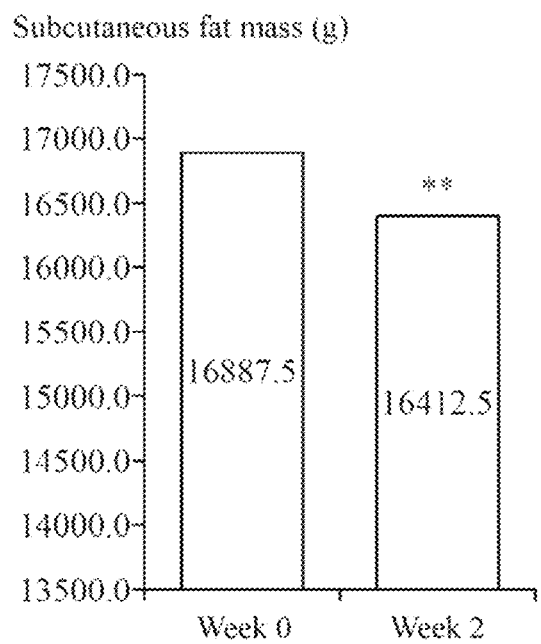
FIG. 11 is a diagram showing detection results of subcutaneous fat mass before taking (week 0) and after taking (week 2) a noni fruit ferment prepared by the method in Example 1.

By the experimental results in FIG. 11, as compared with a subcutaneous fat mass before taking (week 0), the subcutaneous fat mass was reduced by about 475.0 g after taking the noni fruit fermented drink for two weeks.

Figure 12:
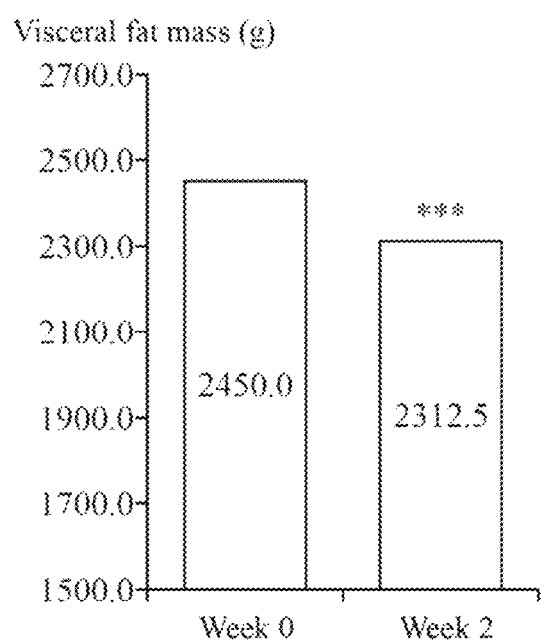
FIG. 12 is a diagram showing detection results of visceral fat mass before taking (week 0) and after taking (week 2) a noni fruit ferment prepared by the method in Example 1.

By the experimental results in FIG. 12, as compared with a visceral fat mass before taking (week 0), the visceral fat mass was reduced by about 137.5 g after taking the noni fruit fermented drink for two weeks.

From above, long-term consumption of the noni fruit fermented drink containing the noni fruit ferment (irradiated by red light) was proven to reduce the (belly and leg) fat accumulation, waist circumference, body fat percentage, and subcutaneous and visceral fat accumulation, and increase the muscle mass; that is, the noni fruit ferment (irradiated with red light) was proven to show the capability in losing weight and improving body shape.

Example 7: Human Subject Experiment—Improving Defecation Status and Improving Gastrointestinal Motility Eight obese subjects (with a body fat percentage greater than 25% or a BML value greater than 24) were allowed to drink a 6 mL noni fruit fermented drink (containing 12 vol % of noni fruit ferment (irradiated by red light) prepared by the method in the Example 1) every day for two weeks. In addition, before taking (week 0) and after taking (week 2), gastrointestinal conditions and defecation status of these subjects were analyzed with a questionnaire.

First, a questionnaire was carried out on the gastrointestinal conditions of these subjects at week 0 (before taking the noni fruit fermented drink) and at week 2 (after taking the noni fruit fermented drink). In detail, a questionnaire was filled out at the two weeks. The symptom items and scores were shown in the following Table 4. Each score represented the severity of each symptom item: 1 represented no abnormality (normal); 2 represented mild; 3 represented ordinary; 4 represented somewhat severe; and 5 represented very severe.

TABLE 4

| Item/Score | 1 | 2 | 3 | 4 | 5 |
|---|---|---|---|---|---|
| 1. Having trouble with constipation |   |   |   |   |   |
| 2. Usual flatulence and indigestion |   |   |   |   |   |

The scores of the questionnaire were converted into questionnaire results in percentage and then averaged and listed in the following Table 5 as well as in FIG. 13 and FIG. 14.

TABLE 5

|   | Week 0 (Average score of subjects) | Week 2 (Average score of subjects) |
|---|---|---|
| 1. Having trouble with constipation | 100.0 | 83.3 |
| 2. Usual flatulence and indigestion | 100.0 | 76.9 |

Figure 13:
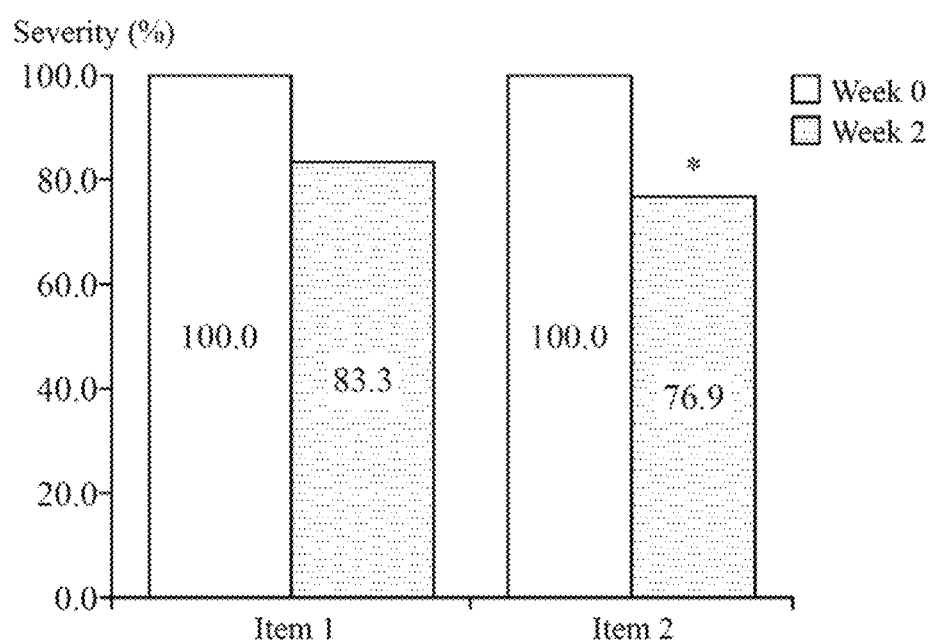
FIG. 13 and FIG. 14 are diagrams showing questionnaire results of defecation status before taking (week 0) and after taking (week 2) a noni fruit ferment prepared by the method in Example 1.
Figure 14:
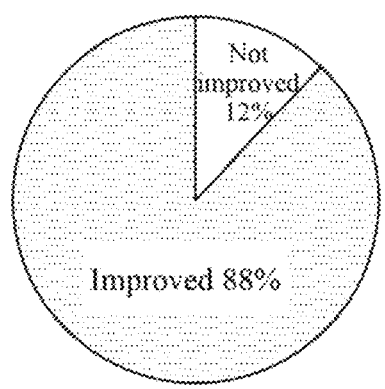

For item 1 (having trouble with constipation) and item 2 (usual flatulence and indigestion), by the questionnaire results in the Table 5 and corresponding FIG. 13, the eight subjects had trouble with constipation and were usually prone to flatulence and indigestion before taking (that is, at week 0). After taking the noni fruit fermented drink (that is, at week 2), the average score for having trouble with constipation was reduced to 83.3 (mild), indicating that, two weeks of taking the noni fruit fermented drink was proven to alleviate constipation. In addition, after taking the noni fruit fermented drink (that is, at week 2), the average score for usual flatulence and indigestion was reduced to 76.9 (mild), indicating that, two weeks of taking the noni fruit fermented drink was proven to alleviate flatulence and indigestion. By the questionnaire results in FIG. 14, after taking the noni fruit fermented drink (that is, at week 2), about 88% of the subjects felt obvious about smooth bowel movement and gastrointestinal motility frequency, indicating that, the noni fruit fermented drink containing the noni fruit ferment (irradiated by red light) was proven to show the capability in improving bowel movement and improving gastrointestinal motility.

Example 8: Human Subject Experiment—Improving Skin Condition

Eight subjects aged from 25 to 40 were allowed to drink a 50 g noni fruit fermented drink (containing 12 wt % of noni fruit ferment (irradiated by red light) prepared by the method in the Example 1) every day for four weeks (i.e., 28 days).

Before drinking (with the face clean, week 0) and 28 days after drinking, values of the facial skin were recorded by using corresponding devices and measurement methods according to different detection items, and photos before and after drinking were taken. (When the detection was carried out before and after drinking, the temperature and humidity of the detection region where the subjects were located were consistent to reduce the influence of external temperature and humidity on the skin).

The skin was detected for the following detection items:

1. Skin Elasticity and Firmness

The skin elasticity detection probe Cutometer® MPA580 (C+K Multi Probe Adapter System, Germany) commercially available from Courage+Khazaka Electronic was used to detect the facial skin of the same subject before and after drinking. The test principle was that, based on the principle of suction and stretching, a negative pressure was generated on the surface of the skin to be tested to suck the skin into a test probe, the depth of the skin sucked into the probe was detected through the optical test system, and the skin elasticity and firmness were calculated by software analysis. An initial value measured by the instrument according to the skin elasticity and firmness was 100%, and a value measured according to the skin elasticity and firmness after four weeks of taking the noni fruit ferment (irradiated with red light) was recorded and then converted and compared with the initial value measured.

2. Quantity and Area of Skin Red Spots

The quantity and area of red spots of these subjects were measured by using a whole face skin quality detector (7th Generation VISIA Complexion Analysis System; Canfield, USA). An initial value measured by the instrument according to the quantity and area of red spots was 100%, and a value measured according to the quantity and area of red spots after four weeks of taking the noni fruit ferment (irradiated by red light) was recorded and then converted and compared with the initial value measured.

3. Skin Spots

The VISIA high-end digital skin quality detector commercially available from Canfield, USA was used to detect the facial skin of the same subject before and after drinking. This detector used UV light and RBX polarized light technology for facial skin photography. Ultraviolet rays could be absorbed by melanin to improve the visibility of pigment spots, so as to detect melanin spots on the epidermis that were invisible. The higher the measurement value was, the more sun spots were. The RBX polarized light could detect melanin spots on the epidermis that were invisible. The higher the measurement value was, the more brown spots were. An initial value measured by the instrument according to the sun spots was 100%, and a value measured according to the sun spots after four weeks of taking the noni fruit ferment (irradiated by red light) was recorded and then converted and compared with the initial value measured.

Figure 15:
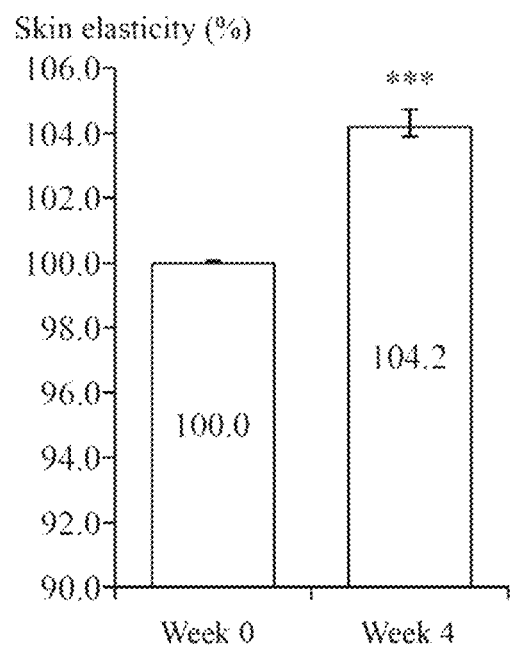
FIG. 15 is a diagram showing detection results of skin elasticity before taking (week 0) and after taking (week 4) a noni fruit ferment prepared by the method in Example 1.

The detection results of "skin elasticity and firmness" of the subjects were shown in FIG. 15. As shown by the experimental results in FIG. 15, as compared with 100% before drinking, after four weeks of drinking the noni fruit fermented drink containing the noni fruit ferment (irradiated by red light), the subjects had a skin elasticity and firmness of 104.2%, increased by about 4.2%. That is, the noni fruit ferment (irradiated with red light) was proven to show the capability in promoting and improving skin elasticity and firmness with the further capability in improving skin appearance and condition by improving skin elasticity.

Figure 16:
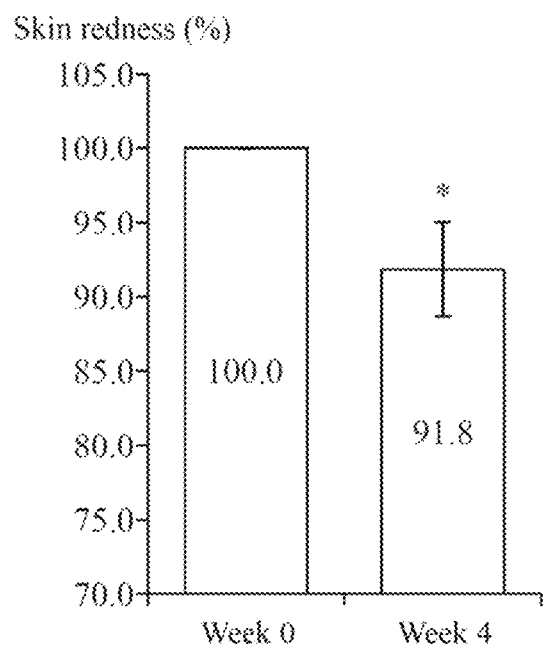
FIG. 16 is a diagram showing detection results of skin redness before taking (week 0) and after taking (week 4) a noni fruit ferment prepared by the method in Example 1.
Figure 17:
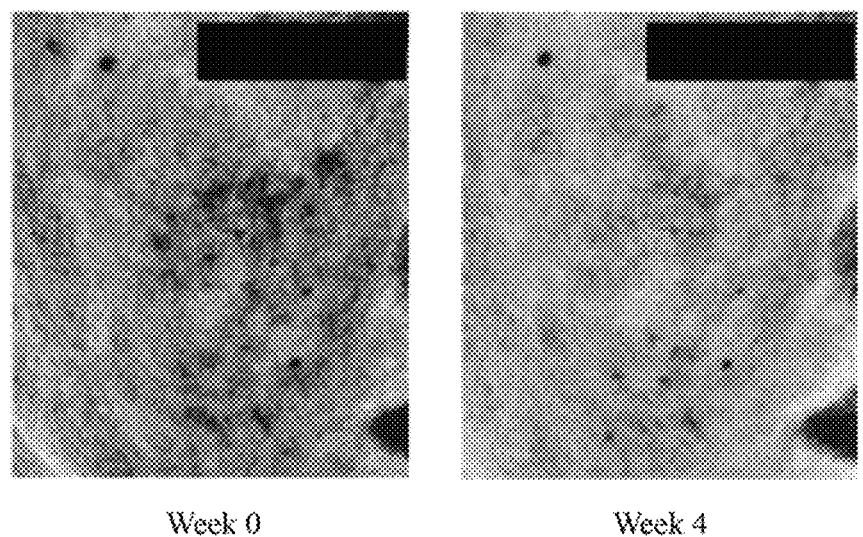
FIG. 17 shows actual detection images showing skin redness before taking (week 0) and after taking (week 4) a noni fruit ferment prepared by the method in Example 1.

The detection results of "quantity/area of skin red spots" of the subjects and actual appearance changes were respectively shown in FIG. 16 and FIG. 17. As shown by the experimental results in FIG. 16, as compared with 100% before drinking, after four weeks of drinking the noni fruit fermented drink containing the noni fruit ferment (irradiated by red light), the subjects had a facial skin redness of 91.8%, reduced by about 8.2%. FIG. 17 showed actual images taken by the detector showing facial skin of a subject at week 0 and at week 4. By FIG. 17, after four weeks of drinking the noni fruit fermented drink containing the noni fruit ferment (irradiated by red light), the subject had the quantity/area of skin red spots significantly reduced. In other words, the noni fruit ferment (irradiated by red light) was proven to show the capability in improving skin appearance and condition by alleviating or lightening skin redness.

Figure 18:
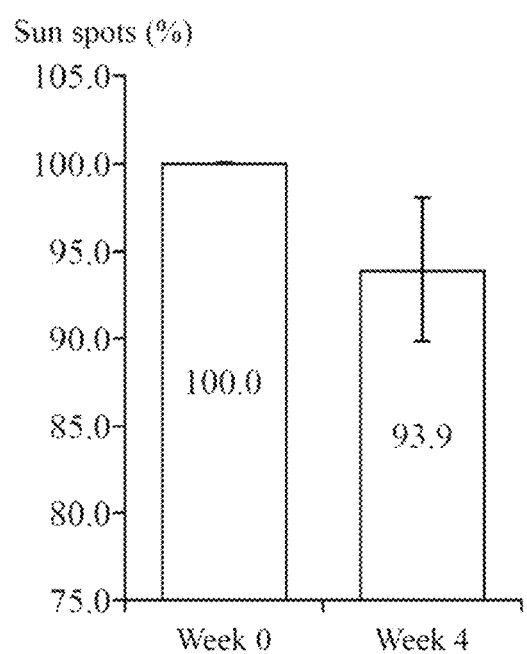
FIG. 18 is a diagram showing detection results of sun spots before taking (week 0) and after taking (week 4) a noni fruit ferment prepared by the method in Example 1.
Figure 19:
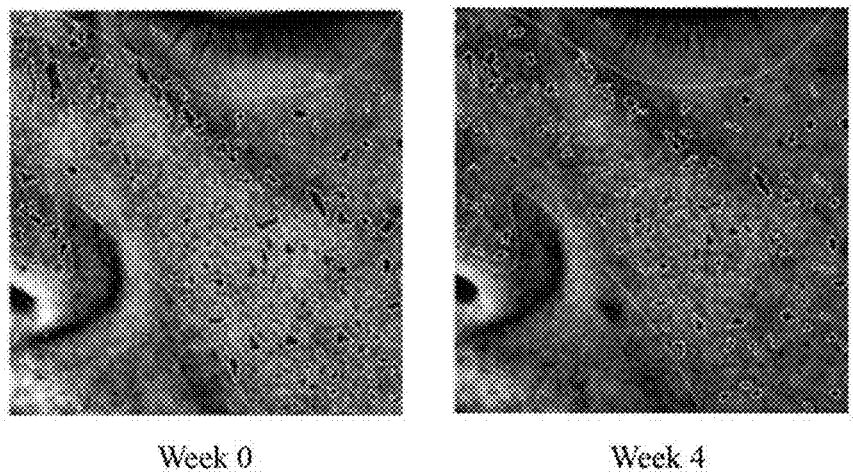
FIG. 19 shows actual detection images showing sun spots before taking (week 0) and after taking (week 4) a noni fruit ferment prepared by the method in Example 1.

The detection results of "skin spots" of the subjects and actual appearance changes were respectively shown in FIG. 18 and FIG. 19. As shown in FIG. 18, as compared with 100% before drinking, after four weeks of drinking the noni fruit fermented drink containing the noni fruit ferment (irradiated by red light), the subjects had sun spots of 93.9%, reduced by about 6.1%. FIG. 19 showed actual images taken by the detector showing facial skin of a subject at week 0 and at week 4. By FIG. 19, after four weeks of drinking the noni fruit fermented drink containing the noni fruit ferment (irradiated by red light), the subject had the quantity/area of sun spots that were significantly reduced. In other words, the noni fruit ferment (irradiated by red light) was proven to show the capability in improving skin appearance and condition by alleviating or lightening sun spots.

Example 9: Human Subject Experiment—Improving Antioxidant Capacity in the Body

Figure 20:
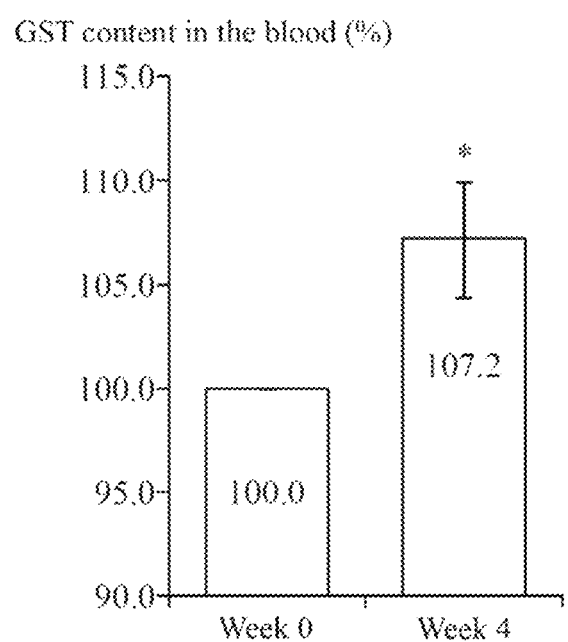
FIG. 20 is a diagram showing detection results of antioxidant capacity in the body before taking (week 0) and after taking (week 4) a noni fruit ferment prepared by the method in Example 1.

Eight subjects aged from 25 to 40 were allowed to take 6 mL of noni fruit ferment (irradiated by red light) prepared by the method in the Example 1 every day for four weeks. Before taking (that is, at week 0) and after taking for 28 days (that is, at week 4), red blood cells in the blood of the subjects were separated with a red blood cell separation medium, the blood of the subjects after separation was adjusted with PBS to $10^6$ cells/mL, and then the activity of glutathione s-transferase (GST) in the red blood cells of human body was measured by biochemical colorimetry, to determine the activity of GST in the blood of each subject. Taking the activity of GST before taking as 100%, the experimental results were shown in FIG. 20.

GST is widely present in various mammalian tissues, and is used to catalyze the conjugation of glutathione (GSH) to the electrophilic group of chemical substances to finally form mercapturic acid to be excreted from the body, which plays an important role in detoxification in the body. GSH-ST has the dual functions of eliminating peroxides and detoxifying in the body. Under the condition of low activity of glutathione peroxides (GSH-PX), GST only has the function of eliminating lipid peroxides (LPO) in the body. As shown by the experimental results in FIG. 20, as compared with 100% before taking, after four weeks of taking the noni fruit ferment (irradiated by red light), the activity of GST in the blood of the subjects was 107.2%, increased by about 7.2%, and the improvement rate was as high as 75% (that is, six out of eight subjects were improved, which was not shown in the figure). That is, the noni fruit ferment (irradiated by red light) was proven to effectively increase the antioxidant indicator enzyme (i.e., GST), thereby improving the overall antioxidant capability in the human body.

The foregoing descriptions are merely examples, and are not intended to become a limitation. Any equivalent modification or change made to the present invention without departing from the spirit and scope of the instant disclosure should fall within the appended claims of this application.

What is claimed is:

1. A method for improving body shape, comprising: administrating to a subject in need thereof a composition comprising an effective amount of a noni fruit ferment prepared by (a) mixing glucose and noni fruit with water for extraction, to obtain a noni fruit broth, and (b) fermenting the noni fruit broth with a plurality of fermenting microorganisms comprising yeast, lactic acid bacteria, and acetic acid bacteria, to obtain the noni fruit ferment, wherein the noni fruit broth and the fermenting microorganisms are simultaneously irradiated by a red light source with a wavelength of 620 nm to 750 nm in the step (b), and the improvement of body shape is at least one of increasing whole body muscle mass, reducing whole body fat percentage, reducing belly fat mass and/or leg fat mass, reducing subcutaneous fat mass and/or visceral fat mass, and reducing waist circumference.

2. The method according to claim 1, wherein the noni fruit ferment contributes to the improving body shape by at least one of promoting leptin production and promoting fat metabolism.

3. The method according to claim 2, wherein the noni fruit ferment contributes to the promoting fat metabolism by increasing an expression level of one or more fat loss genes.

4. The method according to claim 3, wherein the one or more fat loss genes are at least one of adipose triglyceride lipase (ATGL) gene, lipase E (LIFE) gene, and uncoupling protein 1 (UCP1) gene.

5. The method according to claim 1, wherein the noni fruit ferment further has at least one of the following functions: removing free radicals, improving bowel movement, and improving gastrointestinal motility.

6. The method according to claim 1, wherein the glucose is added in an amount of 2 wt % to 8 wt % of a total weight of the noni fruit and the water.

7. The method according to claim 1, wherein a weight of the water is 3 folds to 5 folds of a total weight of the noni fruit.

8. The method according to claim 1, wherein relative to the noni fruit broth, the yeast is added in an amount of 0.01 wt % to 0.5 wt %, the lactic acid bacteria is added in an amount of 0.01 wt % to 0.25 wt %, and the acetic acid bacteria is added in an amount of 1 wt % to 20 wt %.

9. The method according to claim 1, wherein a fermentation time is 24 hours to 72 hours for the yeast, a fermentation time is 24 hours to 72 hours for the lactic acid bacteria, and a fermentation time is 72 hours to 240 hours for the acetic acid bacteria.

10. The method according to claim 1, wherein the noni fruit ferment has a pH value of 2.7 to 3.7 and a Brix degree of 23 to 27.

* * * * *

```
                        SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: ATGL-Forward Primer

<400> SEQUENCE: 1 ggatggcggcatttcagaca                                                    20

<210> SEQ ID NO 2
<211> LENGTH: 21
<212> TYPE: DNA
<213> ORGANISM: Artificial Sequence
<220> FEATURE:
<223> OTHER INFORMATION: ATGL-Reverse Primer

<400> SEQUENCE: 2 caaagggttgggttggttcag                                                   21

<210> SEQ ID NO 3
<211> LENGTH: 20
<212> TYPE: DNA
<213> ORGANISM: Artificial Sequence
<220> FEATURE:
<223> OTHER INFORMATION: LIPE-Forward Primer

<400> SEQUENCE: 3 tggcacaccattttgacctg                                                    20

<210> SEQ ID NO 4
<211> LENGTH: 21
<212> TYPE: DNA
<213> ORGANISM: Artificial Sequence
<220> FEATURE:
<223> OTHER INFORMATION: LIPE-Reverse Primer

<400> SEQUENCE: 4 ttgcggttagaagccacatag                                                   21

<210> SEQ ID NO 5
<211> LENGTH: 21
<212> TYPE: DNA
<213> ORGANISM: Artificial Sequence
<220> FEATURE:
<223> OTHER INFORMATION: UCP1-Forward Primer

<400> SEQUENCE: 5 aggcttccagtaccattaggt                                                   21

<210> SEQ ID NO 6
<211> LENGTH: 22
<212> TYPE: DNA
<213> ORGANISM: Artificial Sequence
<220> FEATURE:
<223> OTHER INFORMATION: UCP1-Reverse Primer

<400> SEQUENCE: 6 ctgagtgaggcaaagctgattt                                                  22

<210> SEQ ID NO 7
```

```
<211> LENGTH: 20
<212> TYPE: DNA
<213> ORGANISM: Artificial Sequence
<220> FEATURE:
<223> OTHER INFORMATION: ACTB-Forward Primer

<400> SEQUENCE: 7 ggctgtattcccctccatcg                                                    20

<210> SEQ ID NO 8
<211> LENGTH: 22
<212> TYPE: DNA
<213> ORGANISM: Artificial Sequence
<220> FEATURE:
<223> OTHER INFORMATION: ACTB-Reverse Primer

<400> SEQUENCE: 8 ccagttggtaacaatgccatgt                                                  22
```